United States Patent [19]

Schroeder et al.

[11] 4,233,227

[45] Nov. 11, 1980

[54] PHTHALIC ANHYDRIDE FORMATION AND SEPARATION

[75] Inventors: Hobe Schroeder, Warrenville; David A. Palmer, Naperville, both of Ill.

[73] Assignee: Standard Oil Company (Indiana), Chicago, Ill.

[21] Appl. No.: 82,069

[22] Filed: Oct. 5, 1979

Related U.S. Application Data

[63] Continuation-in-part of Ser. No. 22,431, Mar. 2, 1979, abandoned.

[51] Int. Cl.$^3$ .............................................. C07D 307/89
[52] U.S. Cl. .............................. 260/346.7; 260/346.4
[58] Field of Search ...................... 260/346.7; 562/414

[56] References Cited

U.S. PATENT DOCUMENTS

| 3,402,184 | 9/1968 | Berthoux | 260/346.4 |
| 3,920,735 | 11/1975 | Wampfler et al. | 260/346.4 |

FOREIGN PATENT DOCUMENTS 856245 12/1960 United Kingdom .

*Primary Examiner*—Henry R. Jiles
*Assistant Examiner*—Bernard Dentz
*Attorney, Agent, or Firm*—Fred R. Ahlers; William T. McClain; William H. Magidson

[57] ABSTRACT

Undesirable discoloration of resultant phthalic anhydride and decomposition thereof and/or o-phthalic acid accompanying dehydration of o-phthalic acid to its anhydride in the presence of oxidation catalyst components Co, Mn and Br can be avoided by the rapid dehydration of o-phthalic acid and rapid vaporization of its anhydride occurring at a reduced pressure of downward from 760 mm Hg down to 40 mm Hg and at a temperature of from 180° C. up to 250° C. under continuous flow conditions which permit rapid removal of anhydride as vapor stream from catalyst components remaining as part of a fluid residue.

4 Claims, No Drawings

PHTHALIC ANHYDRIDE FORMATION AND SEPARATION

PARENT PATENT APPLICATION

This application is a continuation-in-part of U.S. application Ser. No. 22,431 filed Mar. 2, 1979 and now abandoned.

TECHNICAL FIELD

This invention relates to the formation and separation of phthalic anhydride by thermal means from a liquid effluent containing, on a weight basis, from 70% up to 92% o-phthalic acid, from 1.5% up to 21% water, from 0.3 up to 13% benzoic acid, and impurity amounts of oxygen-containing aromatic compounds including precursors of o-phthalic acid, as well as compounds containing cobalt, manganese and bromine derived from the catalysis used for the preparation of such liquid mixture by the air oxidation of liquid o-xylene.

More specifically the present invention pertains to the conditions and extent for heating such liquid mixture to convert its o-phthalic acid content to phthalic anhydride and vaporize the anhydride without enhancing discoloration of said anhydride or its decomposition and/or the decomposition of o-phthalic acid before or during its conversion to its anhydride.

RELATED PATENTS OR PATENT APPLICATIONS

U.S. patent applications Ser. No. 867,050 filed Jan. 5, 1978; Ser. No. 961,763, filed Nov. 17, 1978 and Ser. No. 50,159, filed June 20, 1979, respectively, describe the batchwise and semi-continuous operation, a single-step continuous operation and a continuous two-step operation for the neat oxidation of liquid xylene to provide the liquid effluent used in the present inventive process for the thermal conversion of o-phthalic acid to its anhydride and the separation thereof from attendant water and the remainder of the fluid mixture.

With respect to the understanding and practice of the present inventive process, the fluid mixture containing mainly o-phthalic acid is produced according to the above patent applications by the oxidation of o-xylene with air or air fortified with oxygen gas to an oxygen content of up to 50 volume percent; at a temperature in the range of from 150° C. up to 235° C.; in the presence of a solution of cobalt, manganese and bromine ions as components of catalysis in a solvent comprising o-phthalic acid as a major component, from 3 up to 21 weight percent water also including up to 20 weight percent acetic acid or benzoic acid to make miscible an o-xylene phase and an o-phthalic acid phase otherwise immiscible; and under a gauge pressure in the range of from 17.6 up to at least 28 kg/cm$^2$ to maintain not only a liquid phase of said solution but also to maintain equilibrium conditions favoring retention of o-phthalic acid in the free acid form rather than in the anhydride form. The cobalt component of catalysis is present in an amount based on one gram mole of o-xylene charged of from 0.3 up to 10 milligrams atoms of cobalt. When cobalt is used in amounts less than 0.75 milligram atom per gram mole of o-xylene, zirconium is used in amounts in the range of from 0.2 up to 0.45 milligram atoms per gram mole of o-xylene so that the milligram atom sum of cobalt and zirconium is at least 0.75 milligram atoms per gram mole of o-xylene. With respect to manganese, there are present from 0.5 up to 2 milligram atoms of manganese per milligram atom in the total of cobalt and zirconium milligram atoms. Finally said catalysis has present from 0.5 but less than 2.0 (e.g. 0.5 up to 1.95) milligram atoms of bromine per milligram atom of the total of cobalt, zirconium and manganese milligram atoms used. The advantages from the use of zirconium are the cost reductions arising from use of lower amounts of rather expensive cobalt and the enhancement zirconium contributes to enhancement of maximum rate of oxygen consumption and maintenance of such enhanced rate for a longer time which is important to batchwise and semi-continuous operations wherein rate of oxygen consumption tends to decrease after the first easily oxidized methyl substituent has been oxidized.

Semi-continuous oxidation is a modified batchwise operation comprising three operation modes wherein the middle mode of continuous xylene feed of from 80 to 95% of the xylene separates the batchwise initiation of the air oxidation of 20 to 5% of the xylene in the presence of the total amount of catalyst components to be used and the batchwise conclusion of the oxidation when only air is charged until for all practical purposes oxygen consumption has ceased.

Said related patent applications describe both a continuous single step air oxidation of o-xylene characterized by rather high conversion of o-phthalic acid such that the partially oxidized or intermediate products are of a type which, when separated and recycled to the o-xylene oxidation, do not inhibit, slow, or suppress the oxidation of fresh o-xylene, and a continuous two step oxidation operated in series flow without the need for intermediate separation attendant each step or steps as is associated with the prior art two step oxidation process.

It is in the continuous neat (no extraneous reaction medium solvent) air oxidation of o-xylene that a phase miscibility problem begins to occur when the liquid reaction mixture contains about 40 weight percent o-phthalic acid. At such concentration of o-phthalic acid the o-xylene fed into the liquid reaction mixture becomes insoluble therein or immiscible therewith and forms a separate phase even within the stirred liquid reaction mixture. The catalyst components stay dissolved in the liquid reaction mixture and hence are not as effectively available for the oxidation of o-xylene. The oxidation continues but its vigor diminishes until the rate of oxidation becomes commercially unacceptable. Such vigor diminishing condition is readily observable from the volume ratio of o-xylene to water condensed from the exhaust from the oxidation zone. Such volume ratio is normally in the range of from 0.3:1 to 0.5:1 but the reaction's diminishing vigor is indicated by change of such ratio to 1:1 and finally to 2:1 for an unacceptable reaction rate. However, by continuously adding either acetic acid or benzoic acid to the oxidation zone in an amount of from 5 up to 25, preferably 7 to 10, weight percent of the o-xylene such condition of formation of two distinct immiscible phases does not occur; a commercially acceptable rate of conversion of o-xylene and yield of o-phthalic acid can be obtained by the one step continuous process.

The same problem of formation of two distinct immiscible phases can be overcome simply by use of two series connected oxidation steps. The first oxidation step is conducted under mild conditions to a liquid reaction product containing less than 40 weight percent and preferably less than 25 weight percent o-phthalic acid.

Ideally the extent of oxidation in the first step would be substantially complete conversion of o-xylene with the oxidation products being mainly o-toluic acid with small amounts of 2-carboxybenzylalcohol and 2-carboxybenzaldehyde and no o-phthalic acid. Then the liquid reaction mixture produced by the mild first step is oxidized in a more severe second oxidation step. The difference in severities of the first and second oxidation step can be accomplished by using low temperature in the first step and a combination of high temperature and long residence time in the second step or low temperature and catalyst concentration in the first step and high temperature, higher catalyst concentration and longer residence time in the second step. It is preferred to conduct the first step oxidation of o-xylene at a temperature of 165° C. to 170° C.; under a gauge pressure of 28 to 29 kg/cm$^2$; in the presence of 0.8 to 1.0 milligram atoms of cobalt, 0.4 to 2.0 milligram atoms of manganese and 2 to 8 milligram atoms of bromine per gram mole of o-xylene charged; and for a residence time from 30 to 50 minutes. And to conduct the second step at a temperature of from 212° C. to 215° C.; at a gauge pressure of 28 to 29 kg/cm$^2$; in the presence of from 1.3 to 1.5 milligram atoms of cobalt per gram mole of xylene charged to the first step; a gram atom ratio of Co:Mn:Br in the range of 2:1 to 2:2.5 to 6; charged to the first step; and for a residence time of from 135 to 180 minutes.

In TABLE I below typical compositions are given for the final reaction effluents from acceptable batchwise (Process 1), semi-continuous (Process 2), continuous single step-acetic acid miscibility agent (Process 3a)—benzoic acid miscibility agent (Process 3b), and the continuous two step, no recycle (Process 4) operations.

TABLE I

| Reaction Products Process | 1 | 2 | 3a | 3b | 4 |
|---|---|---|---|---|---|
| o-Phthalic Acid | 88.80 | 91.9 | 71.0 | 76.0 | 91.9 |
| o-Toluic Acid | 0.57 | 0.24 | 1.05 | 1.92 | 1.03 |
| Phthalide | 1.05 | 0.10 | 1.22 | 1.92 | 0.54 |
| 2-Carboxybenzaldehyde | 0 | 0.90 | 0.22 | 0.13 | 0.50 |
| High Boilers | 3.51 | 1.36 | 2.17 | 2.89 | 1.79 |
| Water | 5.0 | 4.9 | 20.50 | 5.75 | 3.45 |
| Benzoic Acid | 0.86 | 0.6 | 0.35 | 11.20 | 0.81 |
| Acetic Acid | 0 | 0 | 3.53 | 0 | 0 |

STATE OF THE ART

No published information was found concerning the dehydration of liquid o-phthalic acid to its anhydride (PAN) in or the separation of a partially purified PAN from the components (Co, Mn, and Br) of oxidation catalysts, the co-products and the by-products of catalytic liquid phase oxidation of o-xylene.

We were aware of the catalytic liquid phase o-xylene oxidation processes of British Pat. No. 856,245 published Dec. 14, 1960 (neat), Example 11 of U.S. Pat. No. 3,920,735 (neat), and U.S. Pat. No. 3,402,184 (in presence of acetic acid). Such oxidation processes result in the direct production of either liquid impure PAN or a solution of PAN in the acetic acid reaction solvent. Neither the British patent nor the two U.S. patents disclose techniques for the separation of PAN from the direct liquid phase reaction product. However the British patent and U.S. Pat. No. 3,402,184 do effect a separation of their PAN products from the oxidation effluents as partially purified o-phthalic acid.

According to the British patent such separation is effected by diluting the oxidation effluent with water, refluxing the mixture for 90 minutes to convert PAN to o-phthalic acid precipitate, recovering said acid by filtration and extracting the filter cake with ether. The extracted filter cake acid was 98% pure.

The PAN separation and recovery process of U.S. Pat. No. 3,402,184 involves water dilution of the acetic acid solution of PAN, boiling the diluted solution to convert PAN to o-phthalic acid which precipitates from the dilute acetic acid, separating therefrom the o-phthalic acid precipitate, thermally converting the separated precipitate back to PAN which was of the quality of only a partially purified product. Such a route to partially purified PAN is not commercially acceptable because of the cost of capital investment and process costs. Also a substantial portion of the o-phthalic acid formed by hydration of first formed PAN remains as solute in the dilute acetic acid solution and must be separated before recovery of acetic acid reaction solvent for its recycle to the oxidation of o-xylene.

Neither of the foregoing techniques for recovery of partially purified PAN are addressed to formation and separation of partially purified PAN from the impure liquid o-phthalic acid products of the types characterized in TABLE I. However, we did heat such liquid impure o-phthalic acid compositions to dehydrate said acid to its anhydride under conditions which would vaporize both the water in such product and water split out to form PAN, the acetic acid when present and the PAN formed, because subjecting the mixed vapors to fractional or partial condensation would be expected to provide separation of a partially purified PAN of relatively high purity. But we found that such thermal conversion of o-phthalic acid to PAN was accompanied by thermal decompositions such that there was a substantial loss of potentially available PAN and the PAN recovered by fractional or partial condensation was a highly discolored product.

Trimellitic acid is produced by catalytic liquid phase air oxidation of pseudocumene in the presence of acetic acid reaction solvent. Since trimellitic acid has a relatively high solubility in acetic acid, the recovery of trimellitic acid therefrom by processes other than crystallization and solid-liquid separation have been proposed. According to U.S. Pat. No. 3,484,458, one of such processes involves evaporation of the acetic acid solvent leaving trimellitic acid in admixture with catalyst (Co, Mn, and Br) components and co-products and by-products of the oxidation. Such mixture was then fed into liquid trimellitic acid anhydride, maintained at a temperature of 232° C. under a sub-atmospheric pressure of 320 mm Hg in a vessel having a reflux condenser operated at a temperature to condense trimellitic acid anhydride and higher boiling materials. The trimellitic acid content of such feed was dehydrated to the intramolecular anhydride in the presence of oxidation catalyst components and the co- and by-products of oxidation. Thereafter a partially purified trimellitic acid anhydride product was evaporated as an overhead fraction from the resulting liquid mixture leaving a bottoms product containing the catalyst components and co- and by-products boiling higher than said anhydride. No mention was made in said U.S. Pat. No. 3,484,458 of thermal decomposition accompanying the dehydration of trimellitic acid or the evaporation of the partially purified anhydride from the resulting mixture.

We adapted the dehydration and anhydride separation process of the above U.S. Pat. No. 3,484,458 to our problem by slowly adding one of the before described (i.e., TABLE I) types of fluid o-phthalic acid products to liquid phthalic anhydride maintained at a temperature of 200° C. and a sub-atmospheric pressure of 100 mm Hg. The vapor mixture (vaporized water and PAN) generated thereby was transported through a side arm condenser cooled to a temperature of 150° C. to condense PAN and materials boiling above 150° C. but to permit vapors of lower boiling materials and water vapor to pass through the condenser. The side arm condenser had a condensate collector. Although the condensate collected had a PAN content substantially equivalent to the o-pthalic anhydride in the feed to the liquid anhydride, such condensate was so discolored that it could not be improved to a commercially acceptable product by heating to a temperature of 250° C. for two hours and then fractionally distilling the product at a sub-atmospheric pressure of 300 to 350 mm Hg.

We noted, when conducting the above adaptation of the dehydration and PAN separation of U.S. Pat. No. 3,484,458, that the first portions of PAN condensate collected appeared to be less discolored than the next and later collected portions. From such observations we devised the following defined concept of the present inventive dehydration of o-phthalic acid to PAN and separations of a partially purified PAN from the components of oxidation catalyst and the co- and by-products of the o-xylene oxidation.

STATEMENT OF THE INVENTION

For the recovery of a partially purified PAN from the liquid effluent containing, on a weight basis, from 70% up to 90% o-phthalic acid, from 1.5 up to 21% water, from 0.3 up to 13% benzoic acid or acetic acid and impurity amounts of oxygen containing aromatic compounds boiling above and below the boiling temperature of PAN including precursors of o-phthalic acid as well as compounds containing cobalt, manganese and bromine derived from the catalysis used for the preparation of such effluent by the neat air oxidation of liquid o-xylene at a temperature of from 150° C. up to 230° C. under a gauge pressure of from 17 up to 30 kg/cm$^2$; the present invention is characterized by the continuous in situ dehydration of o-phthalic acid to PAN and flash evaporation of it from the liquid effluent leaving a fluid residue containing the materials boiling above the boiling temperature of PAN, continuously removing the vapor fraction and the liquid residue fraction as separate streams from the site of such dehydration and flash evaporation, continuously cooling the vapor fraction to a temperature below the boiling temperature of PAN but above the dew point of water and preferably above the melting point temperature of PAN whereby partially purified PAN condenses to the liquid state, and continuously separating the uncondensed vapors from the condensate of partially purified PAN.

Such recovery of partially purified PAN can be suitably effected by introducing the fluid oxidation product into a combination dehydration-evaporation zone maintained at a pressure in the range of from 760 mm down to 40 mm Hg, preferably in the range of from 250 mm down to 100 mm Hg, and at a temperature in the range of from 180° C. up to 250° C.; removing from such zone the separate vapor fraction stream and the liquid residue stream; cooling the vapor fraction in a partial condensation zone operated at a temperature below the boiling but above the melting temperatures of PAN to condense partially purified PAN; and separating the uncondensed portion of the vapor fraction from said PAN condensate.

For efficient fluid flow out of the dehydration-evaporation zone the fluid residue, i.e., a mixture containing materials boiling at a temperature above the boiling temperature of PAN, can contain from 10 up to 60 weight percent PAN as a viscosity reducing flux. Most, 60 to 70%, of said PAN can be recovered as o-phthalic acid of a quality substantially equal to the quality of the partially purified PAN down to quality of the feed to the dehydration-evaporation zone by quenching said fluid residue with water in an amount such that at least an amount equal to the weight of the residue is retained as liquid water at 100° C., cooling the mixture to 20° to 30° C. and filtering the mixture to recove high o-phthalic acid containing insolubles. Such quenching, cooling and filtering process is part of the technique for recovering more than 90 weight percent of the metal components of the oxidation catalyst as solutes in the aqueous filtrate and is further described and disclosed in copending U.S. patent application Ser. No. 968,073, filed Dec. 11, 1978.

The present inventive process is applicable to the liquid efluent product of the neat (no extraneous reaction solvent) liquid phase air oxidation of o-xylene in the presence of catalysis provided by sources of cobalt, manganese and bromine soluble in o-xylene and/or a liquid composition containing 70 up to 92 weight percent o-phthalic acid. As the compositions in TABLE I indicate such fluid effluent in addition to the 70 to 92 weight percent o-phthalic acid also contain from 1.0 up to 21 weight percent water, from 1.3 up to 3.5 weight percent of compounds including components of catalysis boiling at temperatures above the boiling temperature of PAN, from 0.3 up to 13 weight percent benzoic acid, from 0 up to 4.0 weight percent acetic acid, and from 1.2 up to 4 weight percent of precursors (o-toluic acid, 2-carboxybenzoic acid and phthalide) of o-phthalic acid.

The mixture of vapors withdrawn from the heating-vaporizing zone comprises water as the non-organic portion and the organic portion comprising mainly (81–99 wt%) PAN together with benzoic acid and/or acetic acid, the above precursors amounting in toto to from 1.13% up to 1.8% by weight and accompanying bromine-containing compounds in amounts of less than 1000 ppm.

By removing the fraction comprising the mixture of vapors and the fluid metals-containing bottoms fraction from the heating and vaporizing zone substantially as rapidly as such fractions are formed minimizes contact between liquid PAN and the metals containing bottoms fraction. Such minimum contact is an essential critical feature of the present invention. We have found that moderate to relatively long contact between liquid PAN and said metals-containing residue fraction enhances decomposition of PAN thereby lowering its yield and adds, in some way, new colored or color-forming impurities which cannot be removed from PAN by any commercially feasible and economic process. Examples follow of such dehydration wherein there is moderate to long time of contact between the PAN formed and the catalyst metal-containing residue.

The partially purified PAN condensate can be further purified by known methods to a commercially acceptable product whose specification requires a phthalic anhydride content of 99.8% as a minimum, a monocarboxylic acid of 0.1% maximum and a molten color stability value of 50 as a maximum. Said molten color stability is determined by maintaining PAN product at a temperature of 250° C. for 1.5 hours and comparing the color of the liquid PAN side-by-side with a color standard according to ASTM method D2280 using color standards of from 0 up to 1500 described in ASTM method D1209.

Such known methods including heating liquid partially purified PAN to a temperature of from 130° C. up to 285° C. for from 24 up to 48 or more hours followed by two sequential distillations comprising a first simple distillation and a second fractional distillation. The length of the heat treatment step, according to the prior art, can be shortened to from 2 to 12 hours, by the use of various chemical compounds as additives. Such known methods are disclosed, for example, in U.S. Pat. Nos. 2,512,283; 2,671,054; 2,670,325; and 3,155,688.

COMPARATIVE EXAMPLE I

This in situ dehydration of the o-phthalic acid content of effluent from the neat air oxidation of o-xylene is conducted with and in the elements of apparatus comprising a temperature controllable oil bath heated two-necked 500 ml round bottom flask, a downflow condenser, a condensate receiver comprising a temperature controllable oil bath heated two-necked 250 ml round bottom flask, and an up flow condenser connected to an U-tube packed with Rashing rings and wrapped with heating elements so that the tube's legs could be heated to a temperature of 140° C. and melt PAN accumulated on the packing therein. Each packed leg of the U-tube can be operated independently by opening and closing stop cocks in the inverted impacted Y-section whose valved arms are connected to the tops of the U-tube. The leg of said Y-section is connected to an air-cooled trap which is connected to an ice cooled trap which is connected to a third trap cooled by solid $CO_2$ slurry. A vacuum pump is connected to the third trap. The top outlet of the 500 ml flask is connectable to one end of the downflow condenser whose other end is connected to one neck of the 250 ml condensate receiver. The other neck of said receiver is connected to the up flow condenser which in turn is connected to the bottom common inlet for the U-tube.

The oil bath for the 500 ml flask is heated to 200° C. The oil bath of the receiver is heated to 140° C. and oil to be circulated through the downflow condenser and then through the up flow condenser is heated to 150° C. To the 500 ml round bottom flask there are charged 178.9 grams of effluent from the neat air oxidation of o-xylene which contains more than 80 weight percent of o-phthalic acid. Said charged flask is connected to the downflow condenser by way of one neck and the second neck was closed. A sub-atmospheric pressure of 100 mm Hg is imposed on the system of connected apparatus. The 150° C. oil is circulated through the condensers. The U-tubes are operated at 30°–40° C.

After several hours of heating the oxidation reaction effluent to 200° C. only 17.1 grams of partially purified PAN collects in the condensate receiver. The contents of the 500 ml flask is a viscous tarry liquid residue. Since the yield of partially purified PAN is so low, less than one weight percent of the charge, it is not further processed (e.g., by fractionation) to recover PAN of commercial quality.

COMPARATIVE EXAMPLE II

The effluent used in this example is from the neat oxidation of o-xylene and has been cooled to solidify the mixture. Such solid is pulverized and dried to a water content of 0.57 weight percent. The dried, pulverized solid is also found, by analysis to contain, on a weight basis, 0.09% o-toluic acid, 0.05% phthalide, 0.64% 2-carboxybenzaldehyde, 0.6% benzoic acid, 0.33% high boilers, 0.39% Co, 0.18% Mn and 0.74% Br.

The apparatus and procedure used are, except as otherwise noted, the same as used in Comparative Example I. The 500 ml two-necked round bottom flask is charged with 20 grams of commercial quality PAN, connected to the downflow condenser by one neck, and connected to a screw feeder by the second neck. This flask's oil bath is heated to 226° C. A sub-atmospheric pressure of 110 mm Hg is imposed upon the system of apparatus by the vacuum pump. The dried, pulverized reaction effluent is fed into the 500 ml flask by the screw feeder at a rate to maintain the liquid therein at a temperature of 200° C. A small flow of nitrogen gas into the liquid in the 500 ml flask is used to strip PAN and water vapors and to prevent buildup of moist powder at the discharge end of screw feeder. In a five-hour period 403.3 grams of said dried, pulverized oxidation effluent are fed into the heated 500 ml flask. Over the same time period 327.7 grams of liquid condensate are collected in the receiver and 64.9 grams of residue (63.7% PAN by analysis) are accumulated in the 500 ml flask. Said condensate is found by analysis to contain no detectable amount of Co and Mn, 239 ppm bromine, 0.14 wt% o-toluic acid, 0.04 wt% phthalide, 0.02 wt% 2-carboxybenzaldehyde, 0.65 wt% benzoic acid, and 0.02 wt% materials boiling above PAN.

The condensate collected is removed, heated to a temperature of 250° C. for two hours and then fractionated at a sub-atmospheric pressure of 96 mm Hg, a still pot temperature in the range of 210° to 220° C., a condenser temperature of 134° C., a product splitter temperature of 209° to 210° C., a 50:1 reflux ratio for removing a forecut (3.3% of charge), and a 1:1 reflux ratio for product PAN heart cut (80% of charge) recovery collected in 9 portions. The initial color (APHA scale) of each heart cut portion is an almost acceptable 10 to 30 except for the 90 for the first portion. The molten color stability values (APHA color index numbers after each PAN portion held at 250° C. for 90 minutes) for the first eight portions were found to be in the range of 80 to 700. Commercially acceptable PAN has a molten color stability value of not exceeding 50. The composite of said first 8 product portions was found by analysis to contain on a weight basis: 65 ppm Br, 0.01 wt% o-toluic acid, a detectable amount but less than 0.005 wt.% each of phthalide and 2-carboxybenzaldehyde, 0.09 wt% benzoic acid, and 0.23 wt% materials boiling at a temperature above PAN.

The analyses of the partially purified condensate and of the heart cut PAN fraction of said condensate of Comparative Example II indicate that the technique was satisfactory for in situ dehydration of o-phthalic acid content of the effluent of neat air oxidation of o-xylene except for the color and color forming characteristics of the recovered purified product. Also, the change from heating a relatively large mass (178.9 grams) batchwise vis-a-vis heating relatively small mass (1.344 grams per minute) during continuous operation did effect a substantial decrease in thermal decomposition and attendant increase in vaporized partially purified PAN.

The progressive increase in catalyst metals concentration in the retained residue from dehydration and evaporation was suspected as the cause of unacceptable color quality of purified PAN condensate. Based on such concept the procedure and apparatus of Comparative Example II were modified so that accumulation of said dehydration-evaporation residue could be restricted. To test said concept, a new dehydration-evaporation vessel was devised to replace the two necked 500 ml round bottom, oil-bath heated flask used in the above processes.

The new dehydration-evaporation vessel fabricated from glass resembled a double-walled cylindrical Dewar flask whose bottom portion rather than being dished was a double walled cylindrical sump of smaller diameter than the upper portion and whose inner and outer walls were joined with the respective inner and outer walls of the upper portion. An inlet to the space between the two walls was provided through the outer wall near the bottom of the sump. An outlet from the space between the two walls was provided in the outer wall of the vessel's open neck. A constant liquid level maintaining overflow was provided through both walls of said sump for transfer of excess liquid out of said sump to an exterior overflow receiver. Also provided for said sump was a feed inlet through both walls attached to the discharge outlet of a variable intermittent feed cycle ram valve fluid feeder having a 2.54 mm piston to replace the screw feeder. A heated stirred tank is attached to the supply inlet of the ram valve.

It was found that the above fluid feeding system providing a feed fluid at 200°–210° C. and a pressure of 12 to 13 kg/cm$^2$ would not plug in or at the discharge of the ram valve provided the oxidation effluent fluid was diluted with water so that the diluted composition contained from 15 to 25 weight percent water. Other types of feeding systems may not require water dilution of the fluid effluent from the neat air oxidation of liquid o-xylene.

EXAMPLE I

The above dehydration-evaporation vessel with its sump overflow level controller, ram valve feeder and heated stirred tank for feed supply is connected to other apparatus used in comparative Examples I and II by connecting the downflow condenser to the open neck of the dehydrator-evaporator. Hot oil at 226° C. is circulated through the space between the walls of the dehydrator-evaporator. The sump thereof is charged with 50 grams of commercial quality PAN.

The feed for this example is prepared from 400 grams of a composite mixture of several fluid effluents of the neat air oxidations of liquid o-xylene and 100 grams of water which are added to the stirred tank and heated to 200° C. under a gauge pressure of 12.3 kg/cm$^2$. Said composite, on a water-free basis was found, by analysis, to contain on a weight basis: 0.26% Co, 0.42% Mn, 0.22% Br, 0.26% o-toluic acid, 0.04% phthalide, 0.70% 2-carboxybenzaldehyde, 0.87% benzoic acid and 3.15% other impurities including 2.34% of materials (not metal-organo) boiling above PAN.

The ram valve, the transfer line from the stirred tank to said valve and the transfer line from said valve to the sump of the dehydrator-evaporator are heated to, and maintained at, a temperature of 220° C.

The last two traps are filled with their respective coolants. The condenser's circulating oil is heated to 135° C. and its circulation started. The ram valve is adjusted to open and stay open for one second each minute (i.e., open one second and closed 59 seconds). The vacuum pump is turned on, the systems pressure is adjusted to a gauge pressure of 110 mm Hg and the fluid feed was supplied to the ram valve.

During operation of the new dehydrator-evaporator the feed to the sump kept its liquid contents temperature at 195° C. and the inner wall temperature above the sump at a temperature of 204° C. It was noted that each portion of fluid feed entering the sump caused an extensive eruption of liquid, a result of the substantial pressure drop from that of the feed (12.3 kg/cm$^2$) to that of the sump's liquid (110 mm Hg). Such eruptions caused liquid to splash onto the hot wall surface above where PAN formed and evaporated with the water leaving thus leaving a film of residue on the inner wall.

The condensate collected in the condensate receiver amounted to 354.4 grams and upon analysis is found to contain on a weight basis the following impurities: 0.13% o-toluic acid, 0.03% phthalide, 0.09% 2-carboxybenzaldehyde, 0.51% benzoic acid, and 0.24% other impurities which is a total of 1.0% impurities. Said recovered partially purified PAN has a purity of 99%.

Said condensate is heated to and maintained at a temperature of 250° C. for 1.5 hours and then 345.7 grams is distilled batchwise under a sub-atmospheric pressure of 90 mm Hg. A forecut fraction amounting to 2.2 weight percent of the charge is first taken at a reflux ratio of 50:1. Then a heart-cut product fraction is taken in five portions of a 1:1 reflux ratio. The total of the product portions is 271.4 grams (78.5% of the charge). The first two PAN product portions have molten color stability values above the commercial specification of 50 (APHA) but the molten color stability values of the third through fifth portions are 40, 15 and 10 respectively. The composite of the 5 PAN product portions are found by analysis to contain the following concentrations of impurities by weight: 0.04% o-toluic acid, no detectable amounts of phthalide or 2-carboxybenzaldehyde, 0.17% benzoic acid, and 0.10% of other impurities.

In view of the fact that the PAN product recovered at the 1:1 reflux ratio met the commercial purity specifications; at least 99% pure; known effective modifications of the predistillation heating and distillation would provide a product of acceptable molten color value. For example, such color value is known to be improved by heating the partially purified PAN up to 12 hours in the presence, and 24 to 72 hours in the absence of a decolorizing additive in combination with taking a 5% first or forecut fraction during distillation.

The glass double walled dehydration-evaporation vessel used in the process of Example I is replaced by a thin film dehydrator-evaporator having an evaporation surface of 2456 cm$^2$. Said evaporation surface is the surface of a horizontal cylinder rotatable in a tapered jacketed chamber. Said cylinder has on its surface four bladed which have a 1.0 mm clearance from the inner jacket surface. The cylinder rotates at 1800 rpm for a top speed of 10 m/sec. The vapor-liquid disengagement section is heated electrically. The jacket is heated with circulating oil. The jacket is co-extensive with the rotatable cylinder. A flanged glass residue receiver is located in the bottom of the vapor-liquid disengagement zone. The removable tubular vapor outlet contains a glass wool demister pad. The downflow condenser is enlarged to a heat exchange surface of 15300 cm².

EXAMPLE 2

The feed to the above thin film evaporator comprises 1902 grams of liquid oxidation effluent diluted with water so that the liquid feed has a water content of 23 weight percent. The fluid oxidation effluent on a water-free basis comprises the following components expressed in weight percent: 90.7% o-phthalic acid, 0.32% Co, 1.09% Mn, 0.52% Br, 0.11% o-toluic acid, 10 ppm phthalide, 0.29% 2-carboxybenzaldehyde, 1.34% benzoic acid, 1.2% materials boiling below PAN (other than o-toluic acid, phthalide and benzoic acid), and 4.30% materials (not organometallic) boiling above PAN. Said 1902 grams of liquid is maintained at a temperature of 215° C. under a gauge pressure of 28 kg/cm². The ram valve feeder is set to open for one-half (0.5) second and close for 15 seconds. Such operation of the ram valve feeder introduces 22.4 grams per minute of the liquid feed (23% H₂O) into the thin film dehydrator-evaporator which is operated at a temperature of 180° C. and a sub-atmospheric pressure of 100 mm Hg. Hot oil at 220° C. is fed into the jacket of the dehydrator-evaporator. The condenser is operated at a temperature of 137° C. The partially purified PAN condensate is collected in an amount of 1097.9. The residue amounted to 164.4 grams and there was found to be 106.4 grams of materials retained ("hang-up") in the dehydrator-evaporator. Based on analysis said PAN condensate, residue and hang-up contain the components shown in TABLE II.

TABLE II
COMPONENTS OF THREE STREAMS FROM DEHYDRATOR-EVAPORATOR

| Component | PAN Condensate | Residue | Hang-up |
| --- | --- | --- | --- |
| Cobalt (as metal), wt % | 0 | 0.62 | 1.96 |
| Manganese (as metal) wt % | 0 | 1.85 | 5.83 |
| Bromine (as element), wt % | 0.06 | 0.87 | 1.97 |
| o-Toluic Acid, wt % | 0.07 | 0.04 | 0.02 |
| Phthalide, wt. % | 0.007 | 0.001 | 0.02 |
| 2-Carboxybenzaldehyde, wt % | 0.2 | 0.41 | 1.34 |
| Benzoic Acid, wt % | 1.29 | 0.6 | 0.50 |
| Phthalic Anhydride, wt % | 98.5 | 84.5 | 46.3 |
| Low Boilers[1], wt % | 0.1 | 2.3 | 8.39 |
| High Boilers[2], wt % | — | 9.2 | 26.9 |

[1]Materials boiling below (other than o-toluic acid phthalide, benzoid acid) trimellitic acid.
[2]Materials boiling above trimellitic acid.

The above condensate, after being heated to and maintained at 250° C. for 2 hours, is distilled at subatmospheric pressure of 98.5 mm Hg taking a forefraction (5% of charge) at 50:1 reflux ratio and the product fraction at 1:1 reflux ratio. The product fraction amounted to 83.64% of partially purified PAN charged and had, by analysis, a purity of 99.9%.

EXAMPLE 3

A liquid feed is prepared by heating to 200° C. the liquid oxidation effluent (TRE) of the composition shown in TABLE III with water to obtain a feed containing 20 weight percent water. Said liquid feed is maintained at 200° C. under a gauge pressure of 15.5 kg/cm². The apparatus used in this example is the same as used in Example 2. The dehydrator-evaporator is heated to 198° C. with oil entering its jacket at 204° C. The sub-atmospheric pressure on the system is 40 mm Hg. The condenser temperature is 130° C. The ram valve feeder is set to open for 0.5 seconds and stay closed for 20 seconds. The liquid feed amounting to 1828.5 grams was fed into the dehydrator-evaporator in 120 minutes. The condensate collected amounts to 1040 grams, the residue and hang-up were washed from the dehydrator-evaporator with 100 ml of hot water. A small amount of the materials in the dehydrator-evaporator is water insoluble and is dissolved in hot sodium hydroxide. To the resulting alkaline solution there is added acid to a pH of 7. The precipitate that forms is washed with water, and dried and referred to hereafter as "Insolubles."

The above aqueous extract solution is cooled to 24° C. whereat a precipitate forms which is recovered by filtration, washed and dried and is hereafter referred to as "Filter Cake." The analysis of the feed (water free basis), the PAN condensate, the Filter Cake, its attendant filtrate and the Insolubles together with the amounts of the components are shown in TABLE III to provide a material balance and to illustrate the distribution as well as the character and nature of the separated components of the liquid oxidation effluent feed.

With respect to the "wt%" shown for each component in the five compositions in TABLE III, the "wt%" in the "Feed" column is the component's concentration in the liquid effluent feed to the dehydration-evaporation step. However, the "wt%" in the other columns is that portion of the component of the feed appearing in the "Condensate," Filter Cake, Filtrate or Insolubles. Thus said percentage numbers should be read and added across for the material balance of any one component.

TABLE III

| | Feed | | Condensate | | Filter Cake | | Filtrate | | Insolubles | |
| --- | --- | --- | --- | --- | --- | --- | --- | --- | --- | --- |
| Component | Wt. % | Grams | Wt. % | Grams | Wt. % | Grams | Wt. % | Grams | Wt. % | Grams |
| o-Phthalic Acid | 88.8 | 1316 | | | | 162.7 | | 72.98 | | |
| Phthalic Anhydride | | (1173.8)[2] | 85.8 | 1007.6 | 12.4 | (145.1) | 5.5 | (65.1) | | |
| Cobaltous Acetate | 0.83 | 12.24 | | | | | | | | |
| Co-Metal | | (4.08) | | 0.00 | 6.1 | 0.25 | 102.5 | 4.18 | | |
| Manganous Acetate | 1.90 | 28.12 | | | | | | | | |
| Mn Metal | | (8.94) | | 0.00 | 5.9 | 0.53 | 98.7 | 8.83 | | |
| Hydrogen Bromide | 0.31 | 4.66 | | | | | | | | |
| Br Element | | 4.66 | 13.1 | 0.61 | 21.9 | 1.02 | 49.7 | 2.23 | | |
| o-Toluic Acid | 0.82 | 12.09 | 26.2 | 3.17 | 4.9 | 0.59 | 0.7 | 0.08 | | |
| Phthalide | 0.86 | 12.67 | 19.3 | 2.50 | 2.1 | 0.26 | 3.4 | 0.43 | | |
| 2-CBA[1] | 0.54 | 8.01 | 10.7 | 0.86 | 3.7 | 0.30 | 46.8 | 3.75 | | |
| Benzoic Acid | 2.05 | 30.44 | 64.6 | 19.66 | 8.3 | 2.52 | 1.7 | 0.53 | | |
| Dicarboxybenzo-phenone | 0.68 | 10.05 | 4.4 | 0.44 | 12.6 | 1.27 | 90.1 | 9.06 | | |
| Methyl Dicarboxy-benzophenone | 0.68 | 13.11 | 1.8 | 0.23 | 15.7 | 2.06 | 88.9 | 11.66 | 1.9 | 0.19 |

TABLE III-continued

| Component | Feed Wt. % | Feed Grams | Condensate Wt. % | Condensate Grams | Filter Cake Wt. % | Filter Cake Grams | Filtrate Wt. % | Filtrate Grams | Insolubles Wt. % | Insolubles Grams |
| --- | --- | --- | --- | --- | --- | --- | --- | --- | --- | --- |
| Tricarboxybenzo-phenone | 0.83 | 12.23 | 0.3 | 0.04 | 9.2 | 1.12 | 89.2 | 10.91 | 1.7 | 0.21 |
| Other High Boilers | 1.54 | 22.87 | 7.3 | 1.68 | 20.2 | 4.62 | 70.1 | 16.03 | 2.7 | 0.61 |

[1] 2-CBA is 2-carboxybenzaldehyde.
[2] Bracketed number is equivalent of associated component and is not the form of component present.

EXAMPLE 4

A liquid effluent of the type hereinbefore described as obtained from the catalytic (Co, Mn and Br) air oxidation of neat liquid o-xylene is used as feed in the apparatus described in connection with the conduct of the dehydration-evaporation method of Example 3. The liquid feed (1849.9 grams) has a water content of 20 weight percent and is heated to a temperature of 200° C. under a gauge pressure of 10.2 kg/cm$^2$. The dehydrator-evaporator wiped film feed section is operated at a temperature of 224° C. inlet and its vapor-liquid disengagement section is operated at 170° C. under a subatmospheric pressure varying between 40 and 50 mm Hg. The ram valve feeder is set to be open for 0.3 seconds and to be closed for 20 seconds. This permits the 1849.9 grams of feed liquid to be introduced in 90 minutes, or 20.55 grams per minute.

The condensate collected is divided into three portions: A, B and C. The A portion is heated to 250° C. and held at that temperature for 2 hours. The B portion is heated to 300° C. and held at that temperature for 2 hours. The C portion is heated to 250° C. and held at that temperature for 64 hours. Each of the three portions are distilled under sub-atmospheric pressure of 98.5 mm Hg taking a first forerun fraction at a 50:1 reflux ratio and 205° C. temperature followed by taking a product fraction at the reflux ratios of 1:1, 5:1 and 5:1 for A, B and C respectively. The product from portion A has a molten color stability value of 125, from portion B has a molten color stability of 90 and from portion C has a molten color stability value of 40.

Thus, by known procedures the condensate from the present inventive dehydration of o-phthalic acid to PAN and evaporation of PAN can be converted to commercially acceptable PAN.

EXAMPLE 5

The apparatus described with the conduct of Example 3 is used with a liquid feed of 5485 grams containing 65.5 weight percent o-phthalic acid and 17 weight percent water maintained at 200° C. under gauge pressure of 10.2 kg/cm$^2$. Said feed is introduced at a rate of 31.2 grams per minute into the dehydrator-evaporator operated at a sub-atmospheric pressure of 210 to 230 mm Hg, whose wiped film feed section is operated at a temperature of 230° C. and whose liquid-vapor disengagement portion is operated at a temperature of 210° C. The residue which collects amounts to 149 grams and contained 61.2 weight percent PAN. The condensate which collects amounts to 3528 grams and contains 89.85 weight percent PAN and 0.58 weight percent phthalide.

The condensate and 0.32 weight percent thereof of KOH are combined and heated to reflux temperature which is 277° C. Said mixture is refluxed at 277° C. for four hours. From analysis of a sample of such heat treat reaction condensate it is found that such condensate contains no detectable amounts of phthalide. The heat and KOH treated condensate is distilled at a sub-atmospheric pressure of 100 mm Hg taking a first fraction amounting to 5 wt.% at a reflux ratio of 5:1 and then a product fraction at a reflux ratio of 1:1. The product had a molten color stability value of 10 (ASTM Test Method D 1209-69; APHA Pt-Co Color Scale).

The above heat and KOH treatment of partially purified PAN condensate is the subject of copending patent application Ser. No. 898,930, filed Apr. 24, 1978 now U.S. Pat. No. 4,165,324. The use of such chemical and heat treatment of the partially purified PAN obtained by the present inventive process demonstrates the value and merit of said process.

The foregoing examples of the present invention illustrate the use of liquid oxidation effluent at a temperature of from 200° C. to 215° C. and a gauge pressure of from 10 up to 28 kg/cm$^2$ fed to a dehydrator-evaporator operated at a sub-atmospheric pressure of from 40 to 230 mm Hg and a temperature of from 180° C. up to 244° C. with intermittent feed thereto. For continuous feed of the liquid effluent of neat o-xylene oxidation which can be at a temperature as high as 240° C. and a gauge pressure of 30 kg/cm$^2$ there is suitably at least one step of decompression to a gauge pressure in the range of from 5 to 12 kg/cm$^2$ when the liquid feed enters the dehydration-evaporation operated at a sub-atmospheric pressure of 40 to 250 mm Hg. Such decompression can be conducted through a pressure reducer which discharges the decompressed liquid below the surface of the liquid contents in a surge drum. Or the step of decompression can be accomplished by a means analagous to the ram valve feeder used in the Examples herein. Such decompression is useful to avoid the sudden formation of solids and likely attendant plugging of the fluid transfer apparatus elements during decompression of the feed from the gauge pressures of 25 to 30 kg/cm$^2$ down to 40 to 200 mm Hg. Partial decompression for such purpose can be accompanied by water dilution of the liquid oxidation effluent when it contains less than 15 weight percent; e.g. from 3 to 15 weight percent, water. Such dilution can be done by the addition of high pressure steam to the liquid effluent before its decompression to also avoid solidification of the decompressed feed. Dilution for such purposes can be to a water content up to 25, preferably a water content of 17 to 25 weight percent. Such amounts of water in the feed which evaporates with PAN acts to sweep it from the dehydration-evaporation step.

Another mode of practice of the present invention comprises the following procedural steps conducted in the manner and under the conditions described which involve a different concept for decompressing the oxidation reaction effluent.

The flow system used in the following illustrative example has been specially devised to decompress the fluid reaction effluent from either the one step or the two step neat catalytic oxidation of liquid o-xylene with air. It will be appreciated that decompression of such fluid effluents from a gauge pressure of from 17 up to 28 kg/cm² (absolute pressure of from 18 up to 29 kg/cm²) down to a pressure of from 760 down to 40 mm Hg (absolute pressure of from 1.03 down to 0.054 kg/cm²), preferably 250 down to 100 mm Hg, would be accompanied by instantaneous evaporation and resultant precipitation of solids. Such instantaneous precipitation of solids would plug the inlet to the combination dehydration-evaporation zone because there is not sufficient liquid held therein to effectively prevent such solids precipitation upon injection of the fluid effluent below the liquid in said zone. The concept applied in solving said problem associated with the substantial decompression of the fluid effluent feed is to absorb the pressure drop energy by momentum transfer to a circulating liquid.

It will also be appreciated that the heat necessary to dehydrate o-phthalic acid in the oxidation effluent and evaporate its anhydride is not available in the fluid effluent going to the dehydration-evaporation zone. Hence additional heat must be supplied to said zone but must be done in such a manner so that the residence time in said zone and such heat addition do not cause decomposition and added discoloration of the phthalic acid anhydride product. By only dehydrating about 97 to 98% of the o-phthalic acid (PA) to its anhydride (PAN) in said combination zone there is left a rather small amount of fluid containing catalyst component. Such fluid can be rapidly circulated from said combination zone through an indirect heat exchange zone which provides the additional heat and then back into the combination zone. Such circulation for heat addition and retention of a small amount of fluid in a sump to supply such circulation can be accomplished in a total residence time of from 1.0 to 2.0 minutes, an adequately short residence time to avoid the decomposition and added discoloration.

The foregoing concept of absorption of pressure drop energy by momentum transfer can be practiced by injecting the pressurized fluid reaction effluent into the fluid circulating from the combination zone through an external heat exchange zone back to the combination zone.

most (about 99%) of the concentrate produced in the combination dehydration-evaporation zone. The smaller part (0.9 to 1.0%) of the concentrate, here 122.6 kg/hr, is withdrawn and mixed with 7.3 kg/hr of steam at a temperature of 160° C. and an absolute pressure of 5.98 kg/cm². Such mixture is fed to a stirred film evaporation zone operated at a temperature of 227° C. and an absolute pressure of 0.246 kg/cm². From the stirred film evaporation zone there are withdrawn 56.9 kg/hr of residue and 73 kg/hr of vapor mixture containing 95.3% phthalic acid anhydride (PAN). Said vapor mixture is fed into the vapor space above the combination dehydration-evaporation zone.

By injecting the 1231.9 kg/hr of fluid oxidation effluent at a temperature of 214° C. and an absolute pressure of 26.72 kg/cm² into the 13444.7 kg/hr circulating ("cycle") liquid at a temperature of 202° C. and an absolute pressure of 0.246 kg/cm² there is produced a composite feed ("Feed") for the combination dehydration evaporation zone amounting to 14676.6 kg/hr at a temperature of 199° C. and an absolute pressure of 0.492 kg/cm². Said feed is heated by indirect heat exchange to a temperature of 218° C. and thereafter flows into the combination zone operated at an absolute pressure of 0.246 kg/cm². Such operation of the combination zone results in the production of 1109.3 kg/hr of a mixture of vapors and gases containing 77.6 weight percent PAN. Such mixed vapors are combined with the vapors drawn from the wiped film evaporator. The combined mixtures of vapors and gases comprise the "Crude PAN" product of the present illustration of this invention.

The amount (13444.7 kg/hr) of "cycle" liquid might appear to violate the previous caution with respect to long residence exposure to dehydration-evaporation conditions. However, the low volume of such "cycle" liquid held in the combination zone and the high recycle rate of such "cycle" liquid result under the foregoing conditions of a rather low, 1.3 minutes, residence time in said zone as well as in the reheating (indirect heat exchange) zone.

The compositions of the foregoing streams of fluids and mixtures of vapors are shown in TABLE IV to follow.

TABLE IV

| | FLUID STREAMS COMPONENTS, WEIGHT PERCENT | | | | | | |
| --- | --- | --- | --- | --- | --- | --- | --- |
| | | | Dehydration-Evaporation Zone | | | | |
| | | | | Film Evaporator | | | Crude |
| Component | "F.O.E." | "Cycle" | Feed | Feed | Vapor | Residue | PAN Product |
| PA | 59.3 | 9.33 | 13.6 | 9.76 | 0 | 0 | 0 |
| PAN | 23.8 | 51.2 | 48.9 | 53.6 | 87.4 | 33.2 | 78.3 |
| Benzoic Acid | 7.6 | 1.74 | 2.24 | 1.87 | 2.8 | 0.42 | 7.9 |
| o-Toluic Acid | 0.8 | 0 | 0.07 | 0 | 0 | 0 | 0.83 |
| Phthalide | 0.08 | 0.05 | 0.06 | 0.08 | 0.08 | 0.02 | 0.09 |
| High Boilers | 2.7 | 33.2 | 30.6 | 22.6 | 0 | 51.5 | 0.32 |
| o-Xylene | 0.13 | 0 | 0.01 | 0 | 0 | 0 | 0.13 |
| Carbon Oxides | 0.04 | 0 | 0.003 | 0 | 0 | 0 | 0.04 |
| Oxygen | 0.02 | 0 | 0.001 | 0 | 0 | 0 | 0.02 |
| Nitrogen | 0.04 | 0 | 0.004 | 0 | 0 | 0 | 0.04 |
| Co & Mn as Metals | 0.32 | 1.95 | 1.81 | 3.06 | 0 | 6.98 | 0 |
| Bromine | 0.38 | 2.35 | 2.18 | 3.44 | 0 | 7.85 | 0.02 |
| Water | 4.87 | 0 | 0.57 | 0.07 | 9.72 | 0 | 12.30 |

EXAMPLE 6

In this example 1231.9 kg/hr of fluid oxidation effluent ("F.O.E.") produced by the continuous catalytic two-step neat oxidation of liquid o-xylene is decompressed from 26.72 kg/cm² absolute pressure and a temperature of 214° C. by injecting such effluent into 13444.7 kg/hr of circulating ("cycle") fluid which is

The invention claimed is:

1. A method for obtaining a partially purified phthalic anhydride product from the liquid effluent containing from 70 up to 92% o-phthalic acid, from 1.5 up to 21% water, from 0.3 up to 13% benzoic acid and/or acetic acid by weight and impurities boiling above and below the boiling point of phthalic anhydride which are oxygen containing aromatic compounds including precursors of o-phthalic acid as well as compounds containing cobalt, manganese; or bromine derived from the catalysis used for the preparation of such liquid effluent by the neat air oxidation of liquid xylene at a temperature of from 150° C. up to 230° C. under a gauge pressure of from 17 up to 30 kg/cm$^2$; which method comprises the steps of continuous in situ dehydration of o-phthalic acid to phthalic anhydride and flash evaporation of it from said liquid effluent at a pressure of from 760 mm Hg down to 40 mm Hg and a temperature of from 180° C. up to 250° C. leaving a fluid residue fraction containing materials boiling above said anhydride; continuous removal of the vapor fraction and the liquid residue fraction as separate streams from said dehydration-evaporation; continuous removal of heat from the vapor fraction to cool it to a temperature below the boiling temperature of phthalic anhydride but above the dew point of water whereat partially purified phthalic anhydride condenses to the liquid state, and the continuous separation of uncondensed vapors from the liquid partially purified phthalic anhydride condensate.

2. The method of claim 1 wherein the in situ dehydration of o-phthalic acid and evaporation of phthalic anhydride are conducted in a combination dehydration-evaporation zone operated at a temperature in the range of from 180° C. to 250° C. and a sub-atmospheric pressure of from 230 mm Hg down to 40 mm Hg and the vapor fraction is cooled to a temperature of from 130° C. up to 150° C.

3. The method of claim 2 wherein the in situ dehydration-evaporation and cooling of the vapor fraction are conducted under the same pressure of from 230 to 40 mm Hg.

4. The method of claim 2 wherein the liquid oxidation effluent is diluted with water to a liquid composition containing from 15 up to 25 weight percent water and is decompressed in at least one step to a gauge pressure in the range of from 5 to 12 kg/cm$^2$ before charging to the dehydration-evaporation zone.

* * * * *